United States Patent [19]

Hunt et al.

[11] Patent Number: 5,273,545
[45] Date of Patent: Dec. 28, 1993

[54] ENDOSCOPIC CANNULA WITH TRICUSPID LEAF VALVE

[75] Inventors: Robert B. Hunt, Dover; Robert W. Schaefer, Bolton, both of Mass.

[73] Assignee: Apple Medical Corporation, Bolton, Mass.

[21] Appl. No.: 776,194

[22] Filed: Oct. 15, 1991

[51] Int. Cl.5 .......................................... A61M 5/178
[52] U.S. Cl. ................................. 604/167; 604/256; 604/264; 251/149.1; 137/849
[58] Field of Search ............... 604/164, 165, 167, 174, 604/175, 239, 264, 272-274, 256, 245-247, 249; 606/108, 185; 128/DIG. 26, 747; 251/149.1; 137/230, 846, 849

[56] References Cited

U.S. PATENT DOCUMENTS

| | | |
|---|---|---|
| 2,438,457 | 3/1948 | Schlosser . |
| 2,743,119 | 4/1956 | Covert et al. . |
| 2,766,082 | 10/1956 | Ritchey . |
| 3,097,646 | 7/1963 | Scislowicz . |
| 3,127,894 | 4/1964 | Smith . |
| 3,313,299 | 4/1967 | Spademan . |
| 3,454,006 | 7/1969 | Langdon . |
| 3,585,996 | 6/1971 | Reynolds et al. . |
| 3,853,127 | 12/1974 | Spademan . |
| 3,994,287 | 11/1976 | Turp et al. . |
| 4,000,739 | 1/1977 | Stevens . |
| 4,079,738 | 3/1978 | Dunn et al. . |
| 4,177,814 | 12/1979 | Knepshield et al. ................. 604/26 |
| 4,649,904 | 3/1987 | Krauter et al. . |
| 4,655,752 | 4/1987 | Honkanen et al. ................. 604/167 |
| 4,809,679 | 3/1989 | Shimonaka et al. . |
| 4,895,346 | 1/1990 | Steigerwald ......................... 137/849 |
| 4,929,235 | 5/1990 | Merry et al. ......................... 137/849 |
| 5,009,643 | 4/1991 | Reich et al. ......................... 606/185 |

*Primary Examiner*—C. Fred Rosenbaum
*Assistant Examiner*—Ronald K. Stright, Jr.
*Attorney, Agent, or Firm*—Wolf, Greenfield & Sacks

[57] ABSTRACT

A laparoscopic cannula having at its proximal end a resilient end seal carrying a resilient tri-cuspid valve. The valve is passive, yet allows sealing of a body cavity in surgical procedures to prevent fluid flow between the atmosphere and the body cavity, both when an instrument is carried within the cannula and when the cannula is not being used for passage of an instrument to the body.

5 Claims, 2 Drawing Sheets

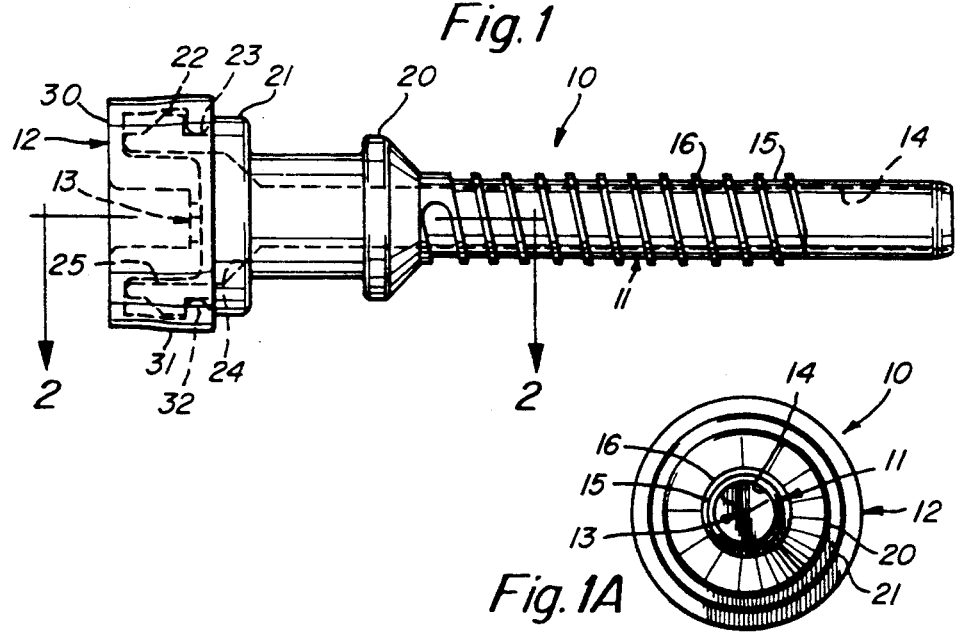
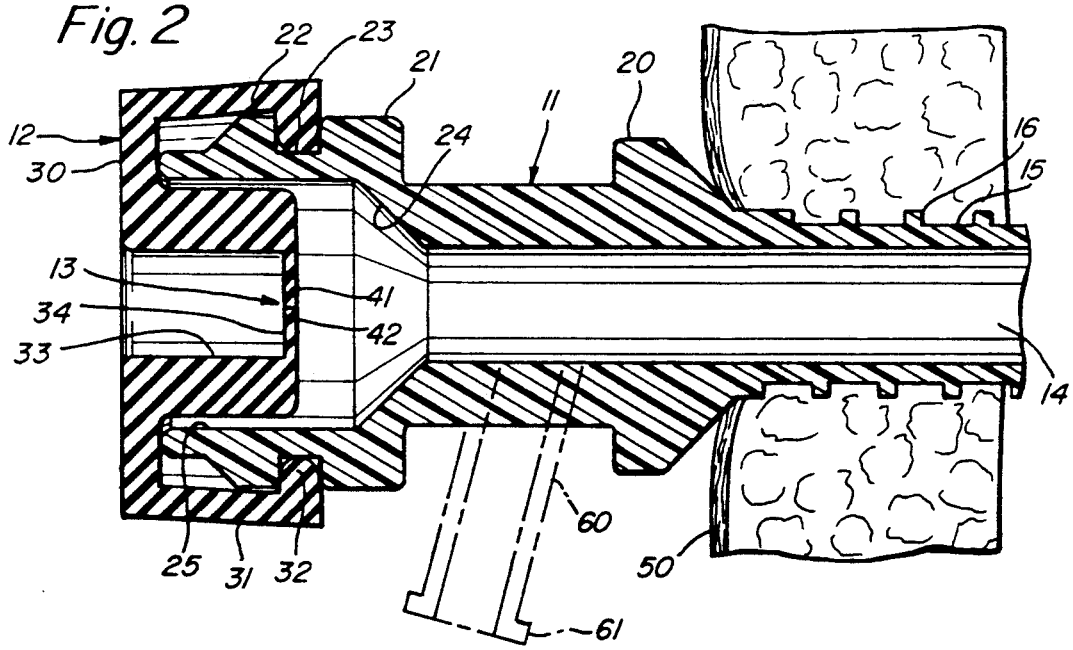
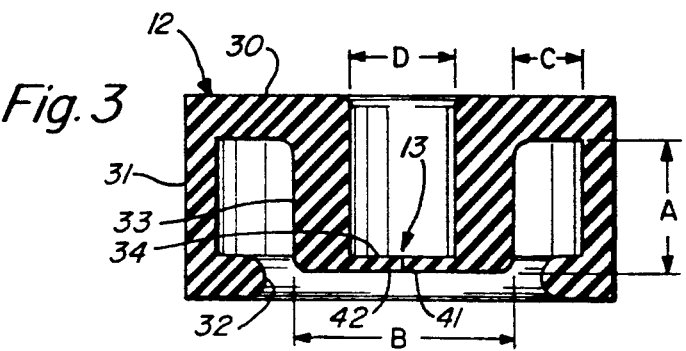

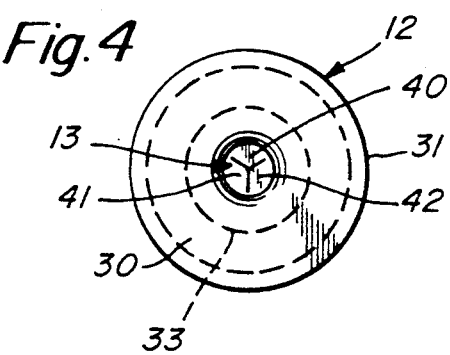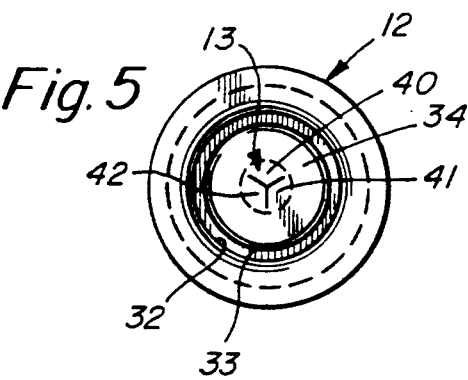

ENDOSCOPIC CANNULA WITH TRICUSPID LEAF VALVE

FIELD OF THE INVENTION

This invention is in the field of endoscopic examination and treatment of the body of mammals, and particularly man. Medical devices are passed into the body through a body wall which, in some cases, must be sealed against fluid flow, both during use of the medical device and thereafter.

BACKGROUND OF THE INVENTION

Endoscopic procedures such as arthroscopy, hysteroscopy and laparoscopy are well known for examination and treatment of internal areas of the body. Often a seal is formed in a cannula passed through a body wall and medical devices which may be viewing or treating devices, as for example, telescopes and surgical cutting devices, respectively, can be used by passage through the seal in the body cavity. In some cases, no seal is necessary, but a seal is useful in those cases where a body fluid or gas, which may naturally occur in the body or be introduced into the body, is required to be sealed from the outside.

In laparoscopy, a medical device such as a telescope is passed through the umbilicus into a distended abdomen. This procedure is commonly used for diagnosis and therapeutic procedures The abdomen is distended by filling the peritoneal space with carbon dioxide to separate the tissue from the organs and provide space to view the organs. Such distention of the abdomen is known as pneumoperitoneum.

The telescope placed into the abdomen is put through a cannula which can be a steel, aluminum, fiberglass or plastic tube with a seal of some sort on the proximal end to prevent loss of gas during the procedure. Very commonly, additional puncture sites are made in the abdomen to allow the passage of an assortment of tools. These secondary cannulas have an assortment of seals at their respective proximal ends to prevent the loss of gas during the procedure.

Seals available for these cannula in the past have often been rubber caps that have circular openings that work only when the instrument is in place, filling the hole or requiring the surgeon or nurse to keep their fingers over the open hole. There are some prior art devices that have both rubber caps and hinged ball valves in combination, eliminating the need for the finger approach. Sliding trumpet valves that are pushed open when an instrument is passed through and stays open because of the instrument have also been used.

More recently, disposable cannulas that have both a rubber cap seal, as well as a flapper valve, have been used as a new approach to a sliding valve allowing sliding of the instrument in use.

In all cases, in laparoscopy and other endoscopic procedures, it is important not to let the distention media such as air or $CO_2$ which has been added, escape from the abdomen or other body cavity. In other procedures where saline or other body fluids must be sealed, it is important to prevent escape of such liquids.

SUMMARY OF THE INVENTION

It is an object of this invention to provide an endoscopic cannula which can be used for laparoscopic or other such procedures for allowing access to a body cavity, and which has a resilient, tri-cuspid leaf valve providing a fluid tight seal at a predetermined area about a medical device or at the seal location, even if the device is not in place, which seal is fluid tight, self forming, reusable and used without adjustment.

Still another object of this invention is to provide a cannula in accordance with the preceding object which is relatively uncomplicated to construct and use in normal surgical procedures and which is capable of automatic sealing in a rapid and efficient manner, with no activation or surgical manipulation or blockage necessary to form the seals.

Still another object of this invention is to provide an integral seal and cap arrangement for mounting at the proximal end of a cannula body as previously described, which cannula body preferably carries means for ease of positive mounting in the body.

SUMMARY OF THE INVENTION

According to the invention, a laparoscopic cannula allows external access to a body cavity in one mode of operation, while preventing fluid flow from the cavity at a designated area during operation of said one mode and also during a second mode of operation where the cavity is sealed without external access. The cannula preferably has a hollow tubular body defining a passageway and having an enlargement at one area thereof designed to be positioned outside of the body. The cannula carries a tri-cuspid resilient leaf valve positioned to close said passageway, yet being yieldable to allow passage therethrough of an elongated device, while sealing the designated area which surrounds the device when said device is used in the body.

In the preferred device, the leaf valve is at the proximal end of the cannula and is maintained in position by a cap integrally formed therewith of a resilient material which is mounted on the proximal end of the cannula. The cannula body has a tubular body which, preferably, has a round outer cross section and a screw thread. The screw thread, preferably, has a square outer flanged threaded area and there is no mold parting line at the land area of the thread so as to permit the cannula to be threaded into the body after use of a trocar as is known in the art. The formation of the screw thread without mold parting lines is an improvement that enables ease of threading and use of the cannula to seal a body opening.

In the preferred embodiment, the tri-cuspid resilient leaf valve is an integral part of the end cap and acts as a single seal for an instrument or device, whether the medical device used with the cannula is in place or not. Additionally, the tri-cuspid valve acts as a gas and/or liquid seal and can act to aid in providing lateral support for an elongated instrument used during the medical procedure.

It is a feature of this invention that because a single seal is used, a surgeon no longer has to be concerned with blocking the passageway when no instrument is in the cannula, nor does he have to park an instrument in the cannula during the procedure to avoid use of his finger to seal the cannula. A single hand can be used in some procedures. The re-entrant profile of the cap can provide a lower profile close to the body which can reduce bulk, clutter and enable desired manipulation of the medical device. The cannula of this invention is formed of a single integral cap carrying the seal which has no separable parts, eliminating the possibility of breaking of the valve and leaving of parts inside of a patient. Since there are no mechanical moving parts, but simply tri-cuspid resilient leaves of soft design, instruments are not damaged when passing through the device and can pass therethrough substantially unimpeded with slight pressure application. Objects such as tools, sutures, needles, electrocautery and telescopic devices can slide easily through the tri-cuspid valve, which can provide lateral support for the instruments in use. An air tight seal is accomplished in both modes of operation of the device and if desired materials are used, low friction surfaces can be presented to medical devices passing through the seal. The seal allows tying of sutures external to the body and passing the sutures and knots through the cannula to be positioned in the abdomen without the loss of pneumoperitoneum. The seal is a passive seal in that no adjustment or manipulation is necessary.

BRIEF DESCRIPTION OF THE DRAWINGS

The above and other object, features and advantages of the present invention will be better understood from a reading of the following specification in conjunction with the accompanying drawings in which:

FIG. 1 is a side plan view of an endoscopic cannula in accordance with the preferred embodiment of this invention;

FIG. 1A is a right end view thereof;

FIG. 2 is a cross-sectional view through a proximal end thereof at line 2—2 thereof;

FIG. 3 is a cross sectional view through a valve cap thereof;

FIG. 4 is a top plan view of the cap of FIG. 3; and

FIG. 5 is a bottom plan view thereof.

DESCRIPTION OF PREFERRED EMBODIMENTS

A laparoscopy cannula in accordance with the preferred embodiment of this invention is shown in FIG. 1 at 10 and comprises a hollow, tubular body 11 and an end cap 12 at a proximal end thereof. The end cap carries a resilient, tri-cuspid leaf valve illustrated generally at 13.

The tubular body 11 is elongated, generally cylindrical and axially extended about an axially extending cylindrical passageway 14. The cylindrical outer surface 15 of the tubular body provides a land surface for a helical thread 16, preferably having a square cross section as best shown in FIG. 1. The shank of the body which forms the outer surface 15 is free of mold parting lines. Thus, as will be described, the tubular body can be screwed through a body wall without parting lines on the land or shank portion 15, creating a stop or irritation to the body as the cannula is screwed into the body. At the proximal end of the cannula, is a first circular flange 20 lying in a plane perpendicular to the central axis of central passageway 14 acting as a stop and gripping member, a second concentric circular flange 21 and a third concentric flange 22 providing an indentation 23 for mounting of the end cap of this invention as will be described.

The tubular body 11 defines the cylindrical passageway 14 which is flared at its proximal end, as indicated at 24, to a wider diameter circular bore 25, to allow entrance of re-entrant end cap 12. The body 11 is preferably formed of a hard plastic material such as Delrin, a trademarked product of DuPont DuNemours of Wilmington, Del., which is resistent to burning by lasers and the like. Other plastics or metals can be used if desired, as for example, stainless steel, polypropylene, nylon, silicone rubber, siloxanes and the like. Preferably, the body 11 is rigid in all conditions of use, but in some cases can be somewhat resilient or pliable.

In the preferred embodiment, the tubular body 11 has an overall length of 3.260" to 3.270" and preferably 3.265"; an outside diameter at the distal end of 0.260" to 0.270" and preferably 0.265"; with a raised screw thread diameter of 0.310" to 0.320" and preferably 0.315". The screw pitch is eight threads per inch. The passageway 14, preferably has a proximal end diameter at 25 of from 0.490" to 0.510" and in the preferred embodiment, 0.500", with a distal end diameter of 0.227" to 0.233" and preferably 0.230".

The body can be opaque or colorless as desired. Preferably, the body is radioluscent. It is preferably made in a single piece, molded and unscrewed from the mold after forming, in order to avoid a parting line which could cause a problem in screwing the cannula into the body.

The end cap 12, as best shown in FIGS. 2-5, comprises a generally cylindrical cross-section having a re-entry right angle cross-section as best shown in FIGS. 2 and 3. Preferably, the end cap is formed of a single, molded piece. Materials useful for the end cap are those that will enable formation of an integral valve and include resilient materials such as NPC 940 commercial grade silicone rubber available from Dow Chemical Company of Midland, Mich. Such material can have a tensile strength of 1050 psi, hardness of 41 Shore A Durometer, elongation of 500% as measured by ASTM D412. Generally Silastic materials are preferred for use (silicone, rubber products produced by Dow-Corning of Midland, Mich.).

It is preferred that the end cap comprise a re entrant cross section, as best shown in FIG. 2. Thus, an end wall 30 has a surrounding cylindrical skirt 31 with a locking tab 32 engaging and snugly fitting the space between flanges 21 and 22 of the tubular body. A re-entrant, cylindrical portion 33 has a distal end wall 34 which carries the re-entrant seal.

As best shown in FIGS. 4 and 5, the re-entrant seal is formed by a tri-cuspid, resilient, leaf valve 13 having tabs 40, 41 and 42. These tabs are designed to provide a gas seal at pressure differentials of from 0 to 20 mm Hg. between the body and the atmosphere when in the position shown in FIG. 4. The seal is enhanced by the thickness of the material at the distal end wall 34, which is preferably 1/32" and preferably from 0.030" to 0.040". The seal can be maintained when a medical device such as an elongated surgical device, telescope or the like is inserted through the seal. When a medical device is inserted through the seal, the seal which is originally flat, as best shown in FIG. 2, or can be slightly cone shaped, is pushed inwardly to expand, yet still maintain a gas and liquid seal between the instrument and the members 40, 41, 42. Thus, the device can be pushed through the seal, manipulated in the body around the end wall of the seal. The cone and enlarged cylinder end of the tubular body can aid in supporting the device for manipulation while maintaining the seal. Withdrawal of the tubular device through the seal leaves the seal intact, both in the passive position shown and the active position when a device is therein.

The tricuspid valve has at least three, preferably equal sized, leaves 40, 41 and 42, but can have more in some cases. For example, four and five or more leave valves having four or five radial slits can be used, so long as the seal remains self-sealing and can seal about a generally cylindrical instrument. All such valves are included in the term "tricuspid valve." Preferably, the slits forming the leaves of such valve define radii of from about 0.0625 inch to 0.120 inch and in the preferred embodiment of 0.08 inch and are 120 degrees apart. Because the tri-cuspid valve is integral with the cap, good contact with the tubular body 11 can be maintained with only a single seal necessary in both modes of use of the device. The unitary nature of the seal and end cap also aids in reducing cost and increasing ease of manufacture, as by molding of a single end cap and cutting of the tri-cuspid tabs of the end seal. The end seal at the tri cuspid valves can be cut, as known in the art. Preferably the end wall has a thickness of from 0.030" to 0.040". This may vary somewhat, depending upon the specific elastomeric material of the end seal.

Other useful elastomeric materials include but are not limited to nylon, polypropylene, polyethylene, polyesters, polyurethanes and other film forming materials, including synthetic organic polymers and copolymerized materials In the preferred embodiment, the end cap is re-entrant, that is, the cylindrical wall portion 33 is provided to pass within the tubular body while the outside flange 31, along with circular locking tab 32, mount the seal on the proximal end. Preferably, the re-entrant distance A is from 0.245" to 0.260", the diameter B is from 0.432" to 0.442", the spacing C is from 0.155" to 0.165", diameter D is from 0.212 to 0.218", with the wall thickness of wall 30 being from 0.059" to 0.066", wall 33 from 0.107" to 0.115", wall 31 from 0.041" to 0.051". Because the wall thickness of wall 33 is preferably maintained greater than the wall thickness of the seal at end wall 34, it is believed that only the end wall 34 allows flexing of the tri-cuspid valve flaps without unwanted bending of other portions of the seal when a device is inserted through the seal and manipulated at angles to its axis. In the preferred embodiment A=0.250", B=0.437", C=0.160", D=0.215", wall thickness of 30 is 0.062", 33 is 0.111", 31 is 0.046" and wall 34 is 1/32".

In use of the cannula of this invention, the cannula is positioned outside the body and a trocar, i.e. a metal, pointed piercing tip, is passed through the cannula out the righthand end as shown in FIG. 2. The peritoneal wall is then pierced by the piercing tip and the tubular body screw threaded into the wall as the piercing tip is withdrawn. The seal 13 prevents exchange of fluids or gases between the body and the atmosphere. The cannula body seals itself around the outside of the tubular portion 11 as the body tissue which has been stretched, compresses about the cannula. Often in a next step when laparoscopic procedures are being performed, carbon dioxide gas can be pumped through another cannula positioned in the body to extend a cavity within the body and allow viewing. In another step, a viewing device such as a telescope is passed through the seal 13 and into the body cavity. Note that the body wall is shown generally at 50 in FIG. 2. After use, the device is simply unscrewed and removed from the body.

At no time does the surgeon performing the operation have to be concerned with sealing the body with his finger or with any external device. The single passive seal provides good sealing. The seal is preferably effective at pressure differentials such as normally encountered in the body and after pumping of a distending gas such as carbon dioxide into the cavity. While laparoscopic procedures have been described, other endoscopic procedures such as hysteroscopy and arthoscopy, where fluids are to be sealed, can be carried out using the cannula of this invention.

In some embodiments of the invention, additional radial entrance passageways can be used to provide additional access to the body. For example, as suggested in dotted outline at 60, 61 of FIG. 1, a side tube 60 can be formed with a Luer lock end 61. This passage is ordinarily sealed by a stopper which can be removed to access the body if desired.

It is a feature of this invention that the design requires no personal manipulation and is a passive seal in that it acts to seal at all times without activation. The seal allows passage of axially extending medical devices of all type, along with sutures if required. It is another feature that the tricuspid valve of this invention can seal a variety of different diameter medical instruments passed therethrough. For example, when the passageway 11 is 5.7 millimeters, the tricuspid valve can seal instruments having diameters of from 1.2 to about 5 mm. Because there is only a small pressure required to insert or withdraw the medical instrument from the tricuspid seal and since the threads form a firm anchor in the body, such instrument can be inserted or withdrawn from the body without holding the cannula 11, thus leaving the practitioner's hands free for other use.

While specific embodiments of the invention have been shown and described, it will be obvious that many variations are possible. For example, the specific length, diameter and sizing of components can vary greatly, depending upon the particular usage desired.

What is claimed is:

1. A laparoscopy cannula for allowing external access to a body cavity in one mode, while preventing fluid flow from said cavity at a designated seal area defined by a tricuspid, resilient, leaf valve, in said one mode, and also preventing said fluid flow during a second mode where said cavity is sealed without external access, said cannula comprising:

a hollow, tubular body defining an elongated passageway and having an enlargement at one area thereof designed to be positioned outside the body, said tubular body carrying an integral closure consisting essentially of a substantially planar wall containing said tricuspid, resilient, leaf valve positioned at said enlargement to close said passageway, yet being yieldable to allow passage therethrough of an elongated medical device while sealing said designated area which surrounds said device while said device is used int he body, said valve being operable without the use of supplementary compression means at said designated area, said tricuspid, resilient, leaf valve being formed of a resilient organic polymeric material having said substantially planar wall comprising an end wall perpendicular to said passageway axis and carried by an end cap mounted on said tubular body having a re-entrant cross-section and an enclosing collar, said re-entrant cross-section defining said planar end wall being mounted on said collar, substantially in a plane perpendicular to said body passageway and carrying said tricuspid leaf valve in said plane perpendicular to said passageway axis, said end wall having a thickness of at least 1/32" and being less than a thickness of said collar.

2. A cannula in accordance with claim 1, and further comprising, said end cap having a resilient outer means for mounting said cap on said hollow tubular body at a proximal end thereof, to permit said cap to have a low profile with respect to a body with which the cannula is used when the cannula is in position for use.

3. A cannula in accordance with claim 2, and further comprising, said passageway being sealed by said tricuspid valve, yet allowing substantially unimpeded passage therethrough of a medical instrument for positioning said cannula in the body and for repositioning of a second medical instrument when said first instrument is withdrawing, with both of said medical instruments being sealed to the surrounding atmosphere and, thus, preventing fluid flow from or into said body at said seal area, and said passageway further defining a flarred portion aligned with said planar end wall.

4. A cannula in accordance with claim 3, wherein said re-entrant end cap defines a guide passageway and a support portion for respectively guiding a medical device and allowing support of said medical device at said seal when said device is positioned to be operative in a body cavity.

5. A laparoscopy cannula in accordance with claim 1 and further comprising, said tubular body defining a helical thread thereon for engagement with a body to seal the body about an outside of said tubular body, said tubular body threaded area being devoid of mold parting lines.

* * * * *